United States Patent
Barnes et al.

(10) Patent No.: US 12,082,785 B2
(45) Date of Patent: Sep. 10, 2024

(54) ENDOSCOPE CLEANING AND FLUSHING ACCESSORY

(71) Applicant: Medivators Inc., Minneapolis, MN (US)

(72) Inventors: Nicolas Barnes, Holmfirth (GB); Mark Jackson, Great Wakering (GB); Kaye Wallace, Shoeburyness (GB)

(73) Assignee: Medivators Inc., Minneapolis, MN (US)

( * ) Notice: Subject to any disclaimer, the term of this patent is extended or adjusted under 35 U.S.C. 154(b) by 557 days.

(21) Appl. No.: 17/433,654

(22) PCT Filed: Mar. 9, 2020

(86) PCT No.: PCT/US2020/021636
§ 371 (c)(1),
(2) Date: Aug. 25, 2021

(87) PCT Pub. No.: WO2020/185643
PCT Pub. Date: Sep. 17, 2020

(65) Prior Publication Data
US 2022/0039643 A1    Feb. 10, 2022

Related U.S. Application Data

(60) Provisional application No. 62/818,218, filed on Mar. 14, 2019.

(51) Int. Cl.
*A61B 90/70* (2016.01)
*A61B 1/00* (2006.01)
(Continued)

(52) U.S. Cl.
CPC .......... *A61B 1/125* (2013.01); *A61B 1/00098* (2013.01); *A61B 90/70* (2016.02);
(Continued)

(58) Field of Classification Search
CPC ..... A61B 1/125; A61B 1/00098; A61B 90/70; A61B 2090/701; A61B 1/00177;
(Continued)

(56) References Cited

U.S. PATENT DOCUMENTS

| | | | |
|---|---|---|---|
| 8,348,906 B2 * | 1/2013 | Tanaka | A61M 25/04 128/207.14 |
| 8,840,733 B2 | 9/2014 | Komiya et al. | |

(Continued)

FOREIGN PATENT DOCUMENTS

| | | | |
|---|---|---|---|
| CA | 3052205 | 8/2018 | |
| JP | 5230247 | 7/2013 | |
| WO | WO-2006023352 A1 * | 3/2006 | ......... A61B 1/00091 |

OTHER PUBLICATIONS

International Search Report and Written Opinion of the International Searching Authority Dated Jun. 5, 2020, of International PCT Application No. PCT/US2020/021636 filed Mar. 9, 2020.
(Continued)

*Primary Examiner* — Michael J Carey
*Assistant Examiner* — Timothy Tuan Luu

(57) ABSTRACT

An endoscope cleansing accessory is described for use at the bedside, manual cleaning sink, or prior to decontamination of the endoscope with an automatic endoscope reprocessing (AER) apparatus. The cleansing accessory includes a cleansing pod or bulbous package filled with a cleaning composition, such as a foam, fluid or powder, and a blocking mechanism located at or near an opening of the cleansing pod. The blocking mechanism is configured to block a suction channel once the cleansing pod is tightly fitted over a distal end of the endoscope. External pressure applied to the outside of the cleansing pod in the form of repeated compression or squeezing drives the cleaning fluid through an elevator platform or forceps raiser bridge mechanism within the endoscope's distal end to loosen tissue and other
(Continued)

particles, which can then be flushed out during manual cleaning or by the flowing cleansing fluid of an AER.

19 Claims, 3 Drawing Sheets

(51) Int. Cl.
*A61B 1/12* (2006.01)
*A61L 2/18* (2006.01)
*A61L 2/26* (2006.01)
*B08B 9/032* (2006.01)

(52) U.S. Cl.
CPC .................. *A61L 2/18* (2013.01); *A61L 2/26* (2013.01); *B08B 9/032* (2013.01); *A61B 2090/701* (2016.02); *A61L 2202/15* (2013.01); *A61L 2202/17* (2013.01); *A61L 2202/24* (2013.01)

(58) Field of Classification Search
CPC ....... A61B 1/05; A61B 1/122; A61B 1/00089; A61B 1/00101; A61B 1/00137; A61B 1/00142; A61B 1/00144; A61B 1/121; A61L 2/18; A61L 2/26; A61L 2202/15; A61L 2202/17; A61L 2202/24; B08B 9/032

See application file for complete search history.

(56) References Cited

U.S. PATENT DOCUMENTS

2009/0215160 A1* 8/2009 Hatori ................ A61B 1/00057
435/287.4
2012/0118338 A1 5/2012 Nakanishi

OTHER PUBLICATIONS

International Preliminary Report on Patentability issued in PCT/US2020/021636, mailed Sep. 23, 2021.

* cited by examiner

ENDOSCOPE CLEANING AND FLUSHING ACCESSORY

PRIORITY CLAIM

This application claims priority and benefit of U.S. Provisional application with Ser. No. 62/818,218, filed Mar. 14, 2019, entitled ENDOSCOPE CLEANING AND FLUSHING ACCESSORY, which is herein incorporated by reference in its entirety.

FIELD AND BACKGROUND

The invention relates generally to cleaning devices and disinfection systems for endoscope devices and other surgical equipment.

Endoscopic devices have been commonly used for various procedures, including the examination and inspection of the interior of body organs, joints or cavities and the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance or for diagnostic procedures, including contrast imaging of biliary or pancreatic ducts. Endoscopes are also frequently used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments) out of the working channel of the endoscope, a rigid elevator or forceps raiser is typically used to orient or deflect the distal end of the wire guide. When the distal end of the wire guide is oriented, the wire guide is inserted into the target anatomy. At this point in the procedure, a catheter or similar treatment instrument can be passed over the wire guide either in a conventional over-the-wire style to the target anatomy.

Additionally, other medical devices such as catheters are disposed through the working channel of an endoscope for various treatments and procedures wherein an elevator is used to position the device at a target location in the patient anatomy. Current endoscopes with elevators or forceps raisers simply actuate or lift the elevator relative to the distal tip of an insertion tube to move the device from one location to another. Even while use of endoscopic instruments is minimally invasive, without proper care, they can still transmit disease. It is necessary that endoscopes be well cleaned and disinfected or sterilized after each use to prevent transfer of potentially dangerous agents between patients. Endoscopes will also often operate in what can be considered a wet environment or other environment where body fluids are in contact with the exterior of the endoscope which is generally a form of rubber tubing. Cleaning and sterilization systems also often utilize liquids in cleaning. Because an endoscope's sophisticated design uses a high number of components which can be adversely affected by moisture, generally an endoscope will be sealed from external fluid invasion by having its components sealed inside the flexible plastic or rubber sleeve. Components which are not sealed during use are alternatively sealed by caps during cleaning as the entire instrument can be inserted in liquid during the cleaning process. To clean endoscopes between procedures, generally the endoscope is first disconnected from associated computer apparatus or endoscope viewing and treatment system, is wiped down and open channels are suctioned and washed to remove most of the material on or within the scope. The scope is then sent to be cleaned or is placed in an automatic endoscope processor (AER) machine or apparatus.

However, with each use of the endoscope and elevator assembly (or forceps raiser bridge mechanism), cleaning and disinfection of the internal working parts becomes more challenging requiring more mechanical manipulation and actuation of the elevator assembly or forceps raiser with disinfecting solutions to ensure residual particles are removed and do not remain lodged therein prior to placement of the endoscope in an AER for final cleaning and disinfecting. Such manual mechanical manipulation of the elevator assembly in the endoscope is time consuming and labor intensive still may not ensure that all tissue and bodily debris is removed from the elevator or forceps raiser. Furthermore, the time gaps between: 1) treatment and manual cleaning; and 2) between manual cleaning insertion into the AER may lead to tissue and debris adhering more firmly to the internal mechanisms and walls of the endoscope, further increasing the difficulty of ensure that the scope is substantially debris-free by the end of AER cleansing.

Therefore there is a need for an endoscope cleaning system that will improve cleaning and disinfection outcomes without increasing health risks to a patient or increasing capital costs due to investments in additional endoscopic equipment or labor costs due to longer manual cleaning times of endoscopes.

SUMMARY

It would be advantageous to reduce labor intensive and time consuming endoscope cleansing processes of endoscopes while improving disinfection outcomes and achieving reduced overall cleaning throughput times without substantially increasing the capital costs of an end user. The invention relates generally to devices and accessories for cleaning and disinfecting elevator platforms or forceps raiser mechanisms of endoscope devices. The various embodiments described herein provide an advantage over the prior art devices and accessories for cleaning of the internal mechanical elevator or forceps raiser mechanisms of endoscopes and preferably before placing them in an automatic endoscope reprocessor (AER) apparatus for a full cleaning and disinfection.

In one example embodiment, an endoscope cleansing accessory is described for use prior to cleaning the endoscope with an automatic endoscope reprocessing (AER) apparatus. The cleansing accessory includes a cleansing pod or bulbous package filled with a cleaning fluid, foam, or powder. The cleaning accessory further includes a blocking mechanism located at or near an opening of the cleansing pod, which is configured to block or shield a suction channel once the cleansing pod is tightly fitted over a distal end of the endoscope, catheter or other medical appliance that is inserted into a patient. External pressure applied to an outside surface of the cleansing pod in the form of repeated compression or squeezing drives the cleaning fluid or composition into an elevator platform or forceps raiser within the endoscope's distal end to loosen tissue and other particles, which are then flushed out by a flowing cleansing fluid of the AER.

In another example embodiment, there is provided an endoscope accessory for use in endoscope reprocessing, the endoscope having at a distal end an elevator platform or forceps raiser assembly and a suction channel inlet disposed adjacent the elevator platform, the endoscope accessory assembly including a cleansing bulbous member configured to be located over the distal end of the endoscope, the bulbous member having an opening configured to be removably fitted over the distal end of the endoscope. The accessory further includes a cleaning composition disposed within the bulbous member and a blocking mechanism configured to block the inlet of the suction channel, wherein pressure applied to an external surface of the bulbous member drives the cleansing composition through elevator platform or forceps raiser within the distal end of the endoscope to loosen tissue and other particles. In this example embodiment, the bulbous member has a shape which facilitates collection of loose tissue and other particle on an internal surface located longitudinally below the bulbous member opening.

In yet another example embodiment there is provided a method of cleaning an endoscope prior to endoscope reprocessing including the steps of providing a cleansing bulbous member having an opening configured to be removably fitted over a distal end of the endoscope, the bulbous member including therein a cleaning composition. The method includes the steps of inserting a blocking mechanism in an inlet of a suction channel of the endo scope and locating the bulbous member opening over the distal end of the endoscope. The method also includes the step of applying pressure to an outside surface of the bulbous member in the form of repeated compression, the repeated compression driving the cleaning composition through the elevator platform to loosen tissue and other particles within the distal end of the endoscope. In this embodiment, the bulbous member has a shape which facilitates collection of loose tissue and other particle on an internal surface located longitudinally below the bulbous member opening.

In yet another embodiment there is provided an endoscope accessory for use in endoscope reprocessing, the endoscope having a distal end, the endoscope accessory assembly including a cleansing bulbous member configured to be located over the distal end of the endoscope, the bulbous member having an opening configured to be removably fitted over the distal end of the endoscope. The accessory includes a cleaning composition disposed within the bulbous member and includes a blocking mechanism configured to block an inlet of a suction channel within the endoscope, wherein pressure applied to an external surface of the bulbous member drives the cleansing composition through the distal end of the endoscope to loosen tissue and other particles. In this embodiment, the bulbous member has a shape which facilitates collection of loose tissue and other particle on an internal surface located longitudinally below the bulbous member opening.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1:
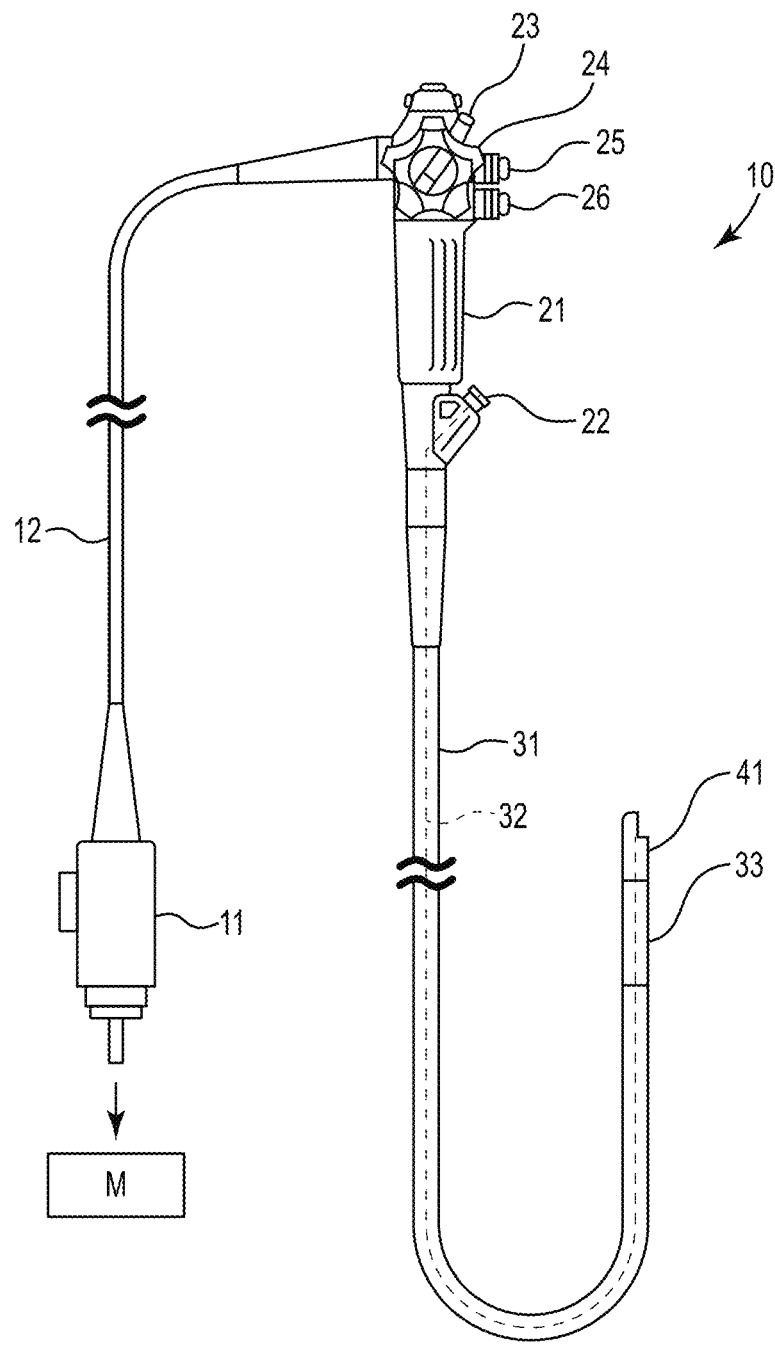
FIG. 1 is a front view of an endoscope having an elevator raiser bridge or forceps raiser mechanism.
Figure 2A:
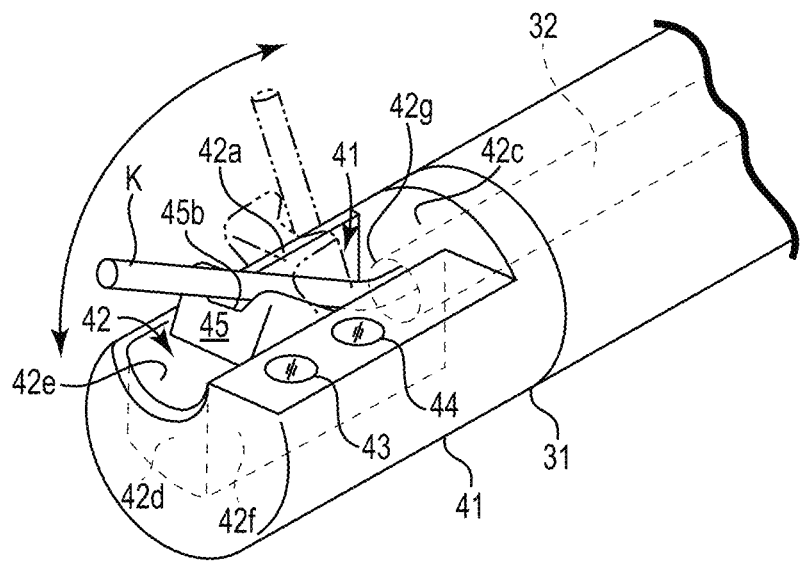
FIG. 2A is a perspective view of a distal end portion of an insertion portion of the endoscope of FIG. 1 and illustrating movement of the elevator raiser.
Figure 3:
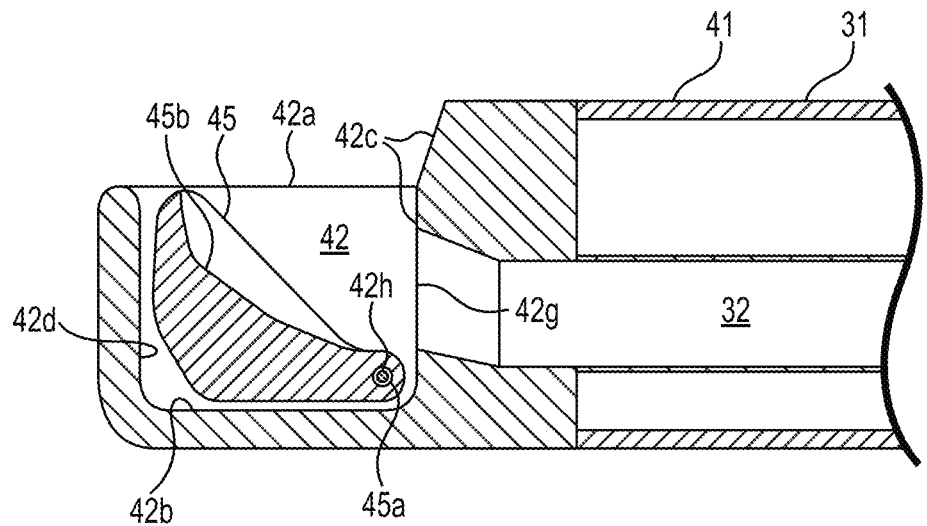
FIG. 3 is a cross-sectional view of the distal end portion of the endoscope illustrated in FIG. 1.

Referring now to FIGS. 1, 2A and 3, in FIG. 1 there is illustrated an endoscope 10 typically connected to an endoscope viewing system. FIG. 2A is a perspective view of a distal end portion 41 of an insertion portion 31 of the endoscope 10. FIG. 3 is a cross-sectional view of distal end portion 41 of the insertion portion 31 of the endoscope 10. In this example, endoscope 10 includes a connector 11, an operation portion 21 and the insertion portion 31 (part typically inserted into patient area to be examined or treated). Connector 11 is configured to be connectable to an endoscope apparatus body or system M. Connector 11 is connected to operation portion 21 via a universal cord 12. Endoscope 10 receives illumination light for illuminating a subject from a light source of the endoscope apparatus body M via connector 11 and outputs an image pickup signal of the subject that is provided by endoscope 10 to the endoscope apparatus body or system M.

Operation portion 21 is typically held by the user and is configured to allow the user to perform various types of operations of the endoscope 10. In this example, operation portion 21 includes a forceps insertion port 22, a forceps raising lever 23, an angle knob or actuator wheel 24, a suction button 25 and an air/water feeding button 26. Forceps insertion port 22 is configured to communicate with a forceps insertion passage or channel 32 and allow the insertion of a forceps device K (FIG. 2A) to protrude from the distal end portion 41 of the insertion portion 31. Forceps raising lever or actuator 23 is connected to a forceps elevator or forceps raiser bridge 45 of distal end portion 41 via a wire (not shown) and can angularly raise or lower forceps or elevator 45 through a turning or rotating operation of actuator 23. Angle knob or actuator wheel 24 is connected to a bending or bendable portion 33 of insertion portion 31 via one or more wires (not shown) and can bend the bending portion 33 through rotating or turning operation of wheel 24. Suction button 25 is operable to suction a suction object from distal end portion 41 through channel 32 or a separate suction channel. Air/water feeding button 26 is operable to send a fluid from a fluid feeding section (not shown) provided to distal end portion 41 through button 26 actuation. Insertion portion 31 includes an elongated section and is configured to be insertable into the patient. Insertion portion 31 includes bending portion 33 configured to be bent by the angle knob 24.

As illustrated in FIGS. 2A and 3, distal end portion 41 of insertion portion 31 includes a concave portion 42, an illumination section or member 43 and an image or camera section 44. Concave portion 42 includes forceps raiser or elevator platform 45 and is configured to allow the forceps device K inserted from forceps insertion port 22 to protrude and move up and down angularly, as indicated by the arrow. Concave portion 42 includes an opening 42a, a base wall 42b, a proximal end side wall 42c formed so as to be perpendicular to base wall 42b, a distal end side wall 42d and both left and right side walls 42e and 42f. Opening 42a is formed on a circumference of distal end portion 41. Each of both left and right side walls 42e and 42f is formed so as to be adjacent proximal end side wall 42c and distal end side wall 42d. Proximal end side wall 42c includes a forceps outlet 42g configured to communicate with the forceps insertion passage 32 formed in side wall 42c. Both the left and right side walls 42e and 42f are each provided with a rotary shaft 42h configured to pivotally support forceps raiser or elevator 45 (FIG. 3).

Forceps raiser or elevator 45 is rotatably attached to rotary shaft 42h through a rotary shaft aperture 45a of the proximal end portion of the forceps raiser. Forceps elevator 45 is typically attached to a wire connected to forceps raising lever 23 at the distal end side of rotary shaft 42h and configured to be rotatable in an upward direction or vertical position toward opening 42a or in a horizontal position pointing toward base wall 42b through the rotation of forceps raising lever 23. Forceps raiser or elevator 45 includes a guide surface 45b formed into a concave curved shape at a position facing forceps outlet 42g. When the forceps device K is inserted from above at forceps insertion port 22, the forceps device K is led out or protrudes out from forceps outlet 42g and forceps raiser or elevator 45 is rotated or turned so as to raise the forceps device, at which time the forceps K is guided along guide surface 45b and protrudes from opening 42a. Hence, forceps raiser 45 is a guide member configured to guide the forceps K that is being used as a treatment instrument, such as taking biopsies or removing abnormal tissue growths in a patient.

Figure 2B:
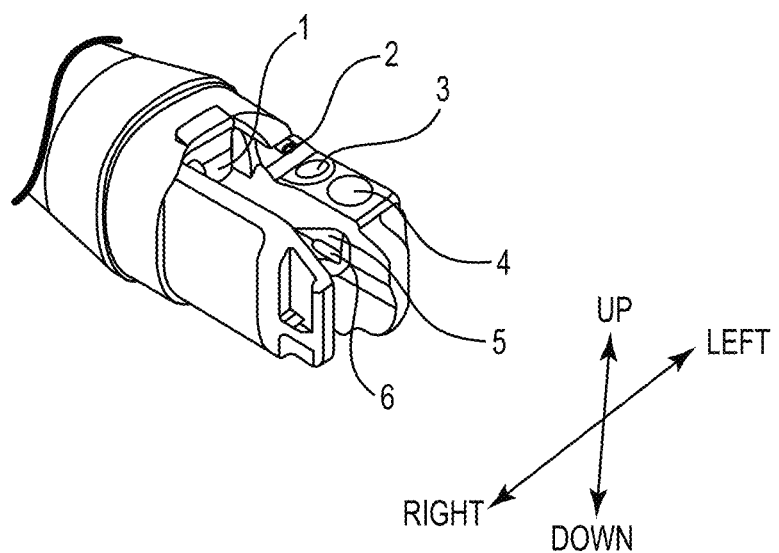
FIG. 2B is a perspective view of a distal end portion of an insertion portion of another endoscope and illustrating movement of the elevator raiser.

Referring briefly to FIG. 2B, is a perspective view of a distal end portion of an insertion portion of another endoscope and illustrating movement of an elevator raiser. In this example embodiment, the endoscope includes a distal end 2 of insertion portion 1, an illumination section or member 3 and an image or camera section 4, an elevator raiser 5 and a wire 6. The cleaning member concept disclosed herein can be fitted over the distal end of the endoscope for cleaning after use on a patient.

Referring again to FIG. 2A, illumination section 43 at distal end 41 of the endoscope is configured to be able to illuminate an area within the patient with light from a light source of the endoscope apparatus body M via connector 11. In this example, image or camera section 44 includes a photoelectric conversion element such as a CCD and is configured to receive reflected light of an area of the patient being examined or treated illuminated by the illumination section 43, thereby photo electrically converting the reflected light and provide an image signal to the endoscope apparatus body M via connector 11. Once treatment or examination of the patient is completed, endoscope 10 is subjected to manual cleaning and then is placed in an automatic endoscope reprocessor (AER) apparatus for a more complete cleaning and disinfecting operation. However, in some instances, a deeper manual cleansing is needed as tissue and body debris may be impacted or wedged in forceps raiser 45, which increases endoscope reprocessing time for the surgical staff and overall cost for the surgical facility and creates an infection control risk.

Figure 4:
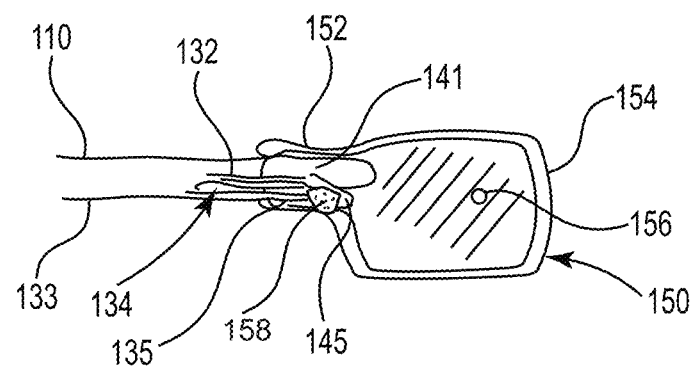
FIG. 4 is a cross-sectional view of a cleansing pod member or cleansing accessory configured to envelope and clean the distal end portion of the endoscope according to the teachings herein.

Referring now to FIG. 4, there is illustrated a duodenoscope 110 being subjected to a pre-automatic endoscope reprocessor (AER) cleansing with a cleansing accessory 150 according to the teachings of the invention. Cleansing accessory 150 is also applicable to other medical appliances, including but not limited to catheters or medical device implanting devices and tools. In this example embodiment, cleansing accessory 150 is configured to envelop a distal portion 141 of insertion portion 133 of the duodenoscope. Duodenoscope 110 further includes an elevator channel 132, a suction channel 134 with a suction channel inlet 135 disposed adjacent an elevator raiser (or forceps) bridge mechanism 145 to be cleansed by cleansing accessory 150. Cleansing accessory 150, in this example embodiment, includes a cleansing bulbous member 154 configured to be located over distal end 141 of duodenoscope 110, bulbous member 154 having an opening 152 configured to be removably fitted over the distal end of the scope. Cleansing accessory 150 further includes a cleaning composition 156 disposed within bulbous member 154. In this example embodiment, a self-puncturing membrane or similar member is located at or near the bulbous member opening 152 such as when member or pod 154 is positioned over the distal end of the endoscope the cleaning composition retained therein will be released.

In other embodiments, cleaning accessory 150 can be configured to clean a re-usable minimally invasive device, such as a forceps, where the distal jaw mechanisms are enclosed by the cleaning accessory 150.

In this example embodiment, cleansing composition 156 is a high level detergent or other disinfecting solution or fluid. In this example embodiment, the chemical composition has a volume of about 30-50 milliliters (ml). The chemical composition and the volume of same in the bulbous member is not limited to this example embodiment and includes other disinfection or bactericidal solutions, such as a foam, in a quantity that is sufficient to clean the forceps or elevator raiser bridge 145. For bedside cleaning solutions (aspiration via suction channel and a basic wipe of patient insertion tube), there is available 250 ml, 300 ml and 500 ml versions).

In this example embodiment, cleansing accessory 150 further includes a blocking mechanism 158 configured to block or shield inlet 135 of suction channel 134, during the cleansing operation with bulbous member 150. In this example embodiment, blocking mechanism 158 is located at or adjacent opening 152 of bulbous member 154 and includes one of a shield or plug member 158 configured to fit over or in inlet 135 of suction channel 134. With bulbous member 154 over distal end 141, pressure applied to an external surface of bulbous member 154 drives cleansing composition 156 through elevator platform or forceps raiser 145 within distal end 141 of the scope to loosen tissue and other particles that may be embedded on the elevator or walls of the concave portion of distal end 141.

In various example embodiments of cleansing accessory 150, bulbous member 154 is formed from one of a translucent or transparent material and is formed from one of a silicone, thermoplastic polymer or rubber material. In a related embodiment, bulbous member 154 has a number of geometric shapes (elliptical, cylindrical, oval, tubular, etc.) that would support holding some chemical composition therein. Further, in a related embodiment, bulbous member 154 includes a drain outlet on an external surface spaced away from opening 152 to facilitate drainage of the cleansing fluid/composition or to be used as another opening to connect the bulbous member or pod to a reservoir (external). In another embodiment, the bulbous member is connected to a flushing line from the AER or other fluid source. In yet another related embodiment, bulbous member 154 includes one or more inlets on an external surface for receiving a cleaning composition from the AER or other fluid sources. In another related embodiment, blocking mechanism 158 is configured to be tethered to bulbous member 154 so as to plug or shield the suction channel inlet before placing bulbous member 154 over distal portion 141 of the duodenoscope. In another embodiment, the blocking mechanism is located at the mouth of opening 152. In yet another related embodiment, blocking (or shielding) mechanism 158 is formed from one of a silicone, thermoplastic polymer or rubber material.

In operation, a method is provided of cleaning an endoscope or medical appliance prior to endoscope reprocessing which includes the steps of providing a cleansing bulbous member 154 having an opening 152 configured to be removably fitted over distal end 141 of the duodenoscope, the bulbous member including therein a cleaning composition 156. Next, the cleaning method includes inserting a blocking mechanism 158 in an inlet 135 of a suction channel 134 of the duodenoscope. Further, the method includes locating bulbous member opening 152 over distal end 141 of the scope and then applying pressure to an outside or external surface of bulbous member 154 in the form of repeated compression, the repeated compression driving cleaning composition 156 through elevator platform or forceps raiser 145 to loosen tissue and other particles within the distal end of the scope. In this example embodiment of the cleaning method, blocking mechanism 158 is located adjacent opening 152 of bulbous member 154 and blocks inlet 135 to the suction channel as bulbous member opening 152 is fitted over the endoscope distal end. In a related embodiment, the method further includes the step of draining the bulbous member via a drain outlet located on the bulbous member surface and spaced away from bulbous member opening 152. In yet another related embodiment, the method further includes the step of providing a second opening to the bulbous member for introducing a cleansing or flushing fluid from an AER.

In another example embodiment, an endoscope accessory for use in endoscope (or catheter or other implanting tool) reprocessing includes a cleansing bulbous member configured to be located over a distal end of the endoscope, the bulbous member having an opening configured to be removably fitted over the distal end of the endoscope or other medical appliance. The bulbous member includes a cleaning composition disposed therein and includes a blocking mechanism configured to block or shield an inlet of a suction channel within the endoscope. In order to commence cleansing of the endoscope or medical appliance, a pressure applied, such as repetitive squeezing or compression, to an external surface of the bulbous member drives the cleansing composition through the distal end of the endoscope to loosen tissue and other particles. Subsequent AER cleansing of the endoscope then flushes out the tissue and debris by the flowing cleansing fluid of the AER. In this example embodiment, the blocking mechanism located at or adjacent the opening of the bulbous member but can also be tethered to the bulbous member for easy access.

The following patents and publications are incorporated by reference in their entireties: U.S. Pat. Nos. 8,182,759; 8,870,005; 9,872,603; US Publication No. 20180310815 and PCT application PCT/JP2014/082536.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. An endoscope accessory for use in endoscope reprocessing, the endoscope having at a distal end an elevator platform or forceps raiser assembly and a suction channel inlet disposed adjacent the elevator platform, the endoscope accessory comprising:
    a cleansing bulbous member configured to be located over the distal end of the endoscope, the bulbous member having an opening configured to be removably fitted over the distal end of the endoscope;
    a cleaning composition disposed within the bulbous member; and
    a blocking mechanism configured to block the inlet of the suction channel, wherein pressure applied to an external surface of the bulbous member drives the cleansing composition through the elevator platform or forceps raiser within the distal end of the endoscope to loosen tissue and other particles,
    wherein the bulbous member has a shape configured to facilitate collection of loose tissue and other particles on an internal surface located longitudinally below the bulbous member opening and wherein the bulbous member includes a self-puncturing membrane located at or adjacent to the bulbous member opening such as when bulbous member is positioned over a distal end of the endoscope the cleaning composition retained therein is released.

2. The endoscope accessory of claim 1, wherein the blocking mechanism is located at or adjacent the opening of the bulbous member.

3. The endoscope accessory of claim 1, wherein the blocking mechanism includes one of a shield or plug member configured to fit over or in the inlet of the suction channel.

4. The endoscope accessory of claim 1, wherein the bulbous member is formed from one of a silicone, thermoplastic polymer or rubber material.

5. The endoscope accessory of claim 1, wherein the bulbous member includes a drain outlet on an external surface.

6. The endoscope accessory of claim 1, wherein the blocking mechanism is formed from one of a silicone, thermoplastic polymer or rubber material.

7. The endoscope accessory of claim 1, wherein the cleaning composition is comprised of at least one of the group consisting of a cleaning detergent, a bactericidal composition, a cleaning foam and a cleansing agent.

8. The endoscope accessory of claim 1, wherein the bulbous member includes an inlet on an external surface for receiving a cleaning composition from an external source.

9. The endoscope accessory of claim 1, wherein the blocking mechanism is configured to be tethered to the bulbous member.

10. A method of cleaning an endoscope prior to endoscope reprocessing comprising the steps of:
   providing a cleansing bulbous member having an opening configured to be removably fitted over a distal end of the endoscope, the bulbous member including therein a cleaning composition and a self-puncturing membrane located at or adjacent to the bulbous member opening;
   inserting a blocking mechanism in an inlet of a suction channel of the endoscope;
   locating the bulbous member opening over the distal end of the endoscope; and
   applying pressure to an outside surface of the bulbous member in the form of repeated compression, the repeated compression driving the cleaning composition through an elevator platform to loosen tissue and other particles within the distal end of the endoscope,
   wherein the bulbous member has a shape configured to facilitate collection of loose tissue and other particles on an internal surface located longitudinally below the bulbous member opening.

11. The method of claim 10 wherein the blocking mechanism is located adjacent the opening of the bulbous member and blocks the inlet to the suction channel as the bulbous member opening is located over the endoscope distal end.

12. The method of claim 10 further comprising the step of draining the bulbous member via a drain outlet located on the bulbous member away from the bulbous member opening.

13. The method of claim 10, further comprising the step of providing a second opening to the bulbous member for introducing a cleansing agent from an external source.

14. An endoscope accessory for use in endoscope reprocessing, the endoscope having a distal end, the endoscope accessory comprising:
   a cleansing bulbous member configured to be located over the distal end of the endoscope, the bulbous member having an opening configured to be removably fitted over the distal end of the endoscope;
   a cleaning composition disposed within the bulbous member; and
   a blocking mechanism configured to block an inlet of a suction channel within the endoscope, wherein pressure applied to an external surface of the bulbous member drives the cleansing composition through the distal end of the endoscope to loosen tissue and other particles, wherein the bulbous member has a shape configured to facilitate collection of loose tissue and other particle on an internal surface located longitudinally below the bulbous member opening and wherein the bulbous member includes a self-puncturing membrane located at or adjacent to the bulbous member opening such as when bulbous member is positioned over a distal end of the endoscope the cleaning composition retained therein is released.

15. The endoscope accessory of claim 14, wherein the blocking mechanism is located at or adjacent the opening of the bulbous member.

16. The endoscope accessory of claim 14, wherein the blocking mechanism includes one of a shield or plug member configured to fit over or in the inlet of the suction channel.

17. The endoscope accessory of claim 14, wherein the bulbous member is formed from one of a translucent or transparent material.

18. The endoscope accessory of claim 14, wherein the bulbous member is formed from one of a silicone, thermoplastic polymer or rubber material.

19. The endoscope accessory of claim 14, wherein the bulbous member includes a drain outlet on an external surface.

* * * * *